(12) United States Patent
Bartholomaeus et al.

(10) Patent No.: US 7,994,382 B2
(45) Date of Patent: Aug. 9, 2011

(54) APPLICATION SYSTEM FOR A PLASTER CONTAINING AN ACTIVE INGREDIENT AND A CONTROLLED-RELEASE AGENT FOR SAID ACTIVE INGREDIENT

(75) Inventors: Johannes Bartholomaeus, Aachen (DE); Heinrich Kugelmann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 815 days.

(21) Appl. No.: 12/066,216

(22) PCT Filed: Aug. 25, 2006

(86) PCT No.: PCT/EP2006/008366
§ 371 (c)(1),
(2), (4) Date: Mar. 7, 2008

(87) PCT Pub. No.: WO2007/028513
PCT Pub. Date: Mar. 15, 2007

(65) Prior Publication Data
US 2008/0274146 A1    Nov. 6, 2008

(30) Foreign Application Priority Data
Sep. 9, 2005   (DE) .................... 20 2005 014 347 U

(51) Int. Cl.
*A61F 13/00*    (2006.01)
(52) U.S. Cl. ............ 602/48; 424/448; 424/449; 602/41; 602/42; 602/57; 602/58
(58) Field of Classification Search .............. 602/48, 602/57–59, 41, 42; 604/304–308; 206/441; 424/448, 449, 443; D24/189
See application file for complete search history.

(56) References Cited

U.S. PATENT DOCUMENTS

| | | | |
|---|---|---|---|
| 4,917,688 A | 4/1990 | Nelson et al. | |
| 4,925,670 A | 5/1990 | Schmidt | |
| 5,801,201 A | 9/1998 | Graudums et al. | |
| 6,221,384 B1 | 4/2001 | Pagedas | |
| 6,248,737 B1 | 6/2001 | Buschmann et al. | |
| 2003/0125659 A1 | 7/2003 | Fleischer | |
| 2005/0249792 A1 | 11/2005 | Kugelmann | |

FOREIGN PATENT DOCUMENTS

| | | |
|---|---|---|
| DE | 36 30 603 A1 | 3/1988 |
| DE | 197 33 981 A1 | 2/1999 |
| DE | 199 00 645 A1 | 7/2000 |
| DE | 102 13 772 A1 | 10/2003 |
| DE | 10 2004 020 463 A1 | 11/2005 |
| EP | 0 249 475 A2 | 12/1987 |
| EP | 0 581 057 A1 | 2/1994 |

(Continued)

OTHER PUBLICATIONS

Corresponding International Search Report (Form PCT/ISA/210) dated Feb. 27, 2007 including Form PCT/ISA/220 and Form PCT/ISA/237 with English translation of relevant portion (Fourteen (14) pages).
Corresponding German Search Report dated Dec. 6, 2005 with English translation of relevant portion (Nine (9) pages).

(Continued)

*Primary Examiner* — Kim M Lewis
(74) *Attorney, Agent, or Firm* — Crowell & Moring LLP

(57) ABSTRACT

The present invention relates to an application system for an active ingredient release system, comprising a film-form application strip, which is in each case bonded detachably to an active ingredient-containing plaster and a separate active ingredient release regulator separate there from.

18 Claims, 1 Drawing Sheet

FOREIGN PATENT DOCUMENTS

| | | | |
|---|---|---|---|
| EP | 0693 475 | B1 | 1/1996 |
| EP | 0 780 369 | B1 | 6/1997 |
| WO | WO 88/05293 | A1 | 7/1988 |
| WO | WO 02/41878 | A2 | 5/2002 |
| WO | WO 2005/025549 | A2 | 3/2005 |

OTHER PUBLICATIONS

Corresponding International Preliminary Examination Report (Form PCT/IPEA/409) dated Nov. 21, 2007 including Form PCT/IPEA/416 with English translation of Amended Sheets (Fifteen (15) pages).
The English translation of the International Preliminary Report on Patentability (Seven (7) pages), Jul. 23, 2008.

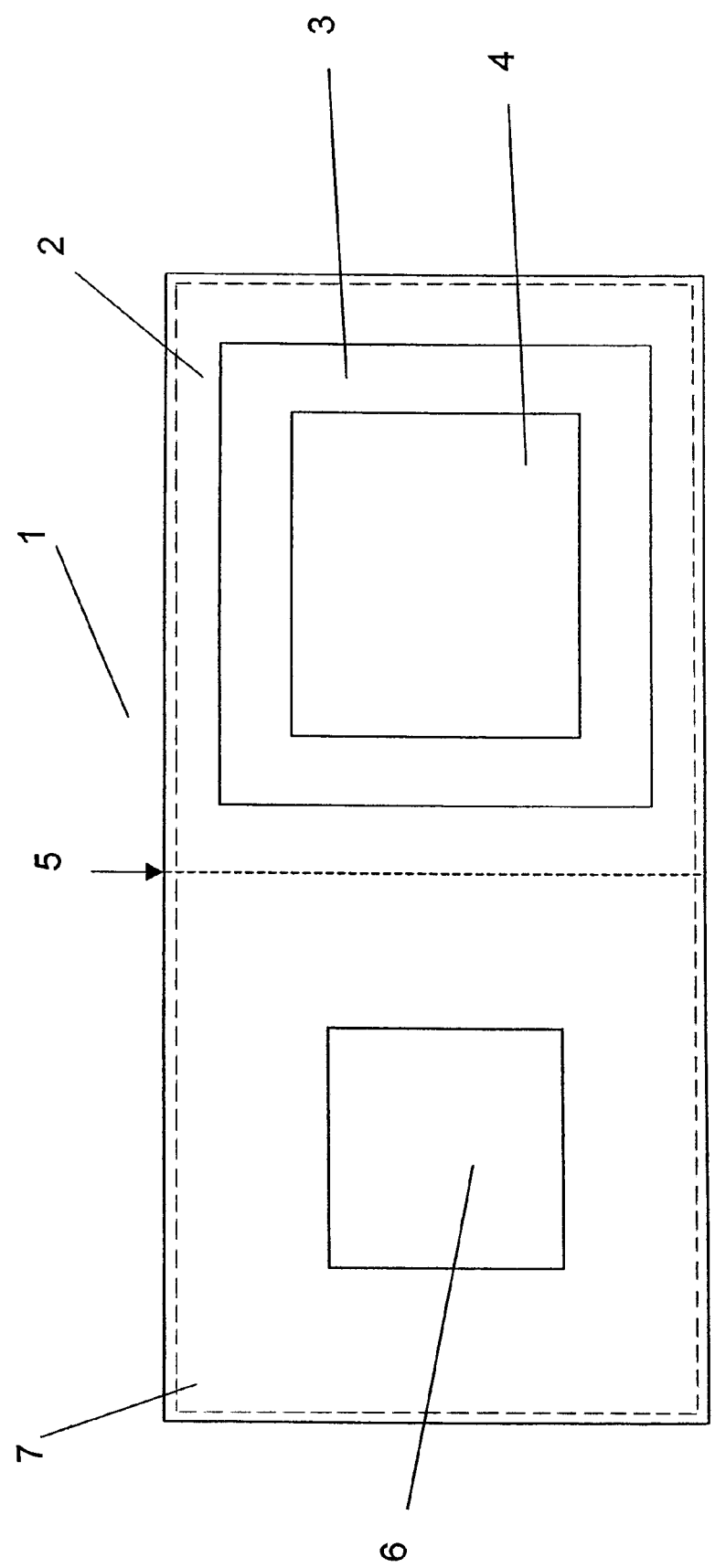

APPLICATION SYSTEM FOR A PLASTER CONTAINING AN ACTIVE INGREDIENT AND A CONTROLLED-RELEASE AGENT FOR SAID ACTIVE INGREDIENT

The present invention relates to an application system for an active ingredient release system, comprising a film-form strip, an active ingredient-containing plaster bonded detachably thereto and an active ingredient release regulator likewise bonded detachably thereto and separate from the active ingredient-containing plaster, the film-form strip having a width which corresponds at least to the width of the active ingredient-containing plaster and to a width optionally extending therebeyond of the peelable protective film used to cover the adhesive surface of the active ingredient-containing plaster and the length of the strip being a multiple of the length of the plaster and comprising a fold line, whereby the active ingredient release regulator may be positioned after removal of the protective film peelable therefrom on the active ingredient-containing surface of the plaster after removal of its protective film by folding the strip back together and the plaster provided with the active ingredient release regulator may be applied directly to the skin with removal of the strip.

Topical or systemic release of an active ingredient via the skin into the human or animal body conventionally proceeds in that the active ingredient is absorbed by the skin via the contact surface with the skin.

In the process, the active ingredient is thus conventionally released over the entire contact surface of the active ingredient-containing area of a plaster.

To achieve tailored dosage of the active ingredient using such preferably transdermal administration, in the case of known matrix plasters containing active ingredient the active ingredient-containing area of a plaster has to be reduced in size, e.g. by cutting. This generally results in inexact dosage. Plasters which have the active ingredient available in a reservoir are unable to provide tailored dosage in this way.

This also applies to the tailored dosage option described in US 2003/0125659 for plasters containing active ingredient which contain the active ingredient embedded in a matrix. A disadvantage of the dosage systems described therein is that suitable dosage is only obtained from plasters with a specific predetermined width which corresponds to the outlet of the dosage device. Corresponding use of the various commercially available matrix plasters of any design containing active ingredient is not possible according to this known dosage system.

Furthermore, limited tailored dosage provided by a transdermal therapeutic system is known from DE 197 33 981, a given active ingredient-containing area of a matrix plaster being covered with a cover layer impermeable to the active ingredient. The system merely provides a one-off possibility for reducing the tailored dose of transdermal active ingredient released.

An active ingredient release system for matrix or reservoir plasters of any design containing active ingredient, which allows tailored dosage of the active ingredient adapted to the patient, e.g. to body weight, is disclosed in German patent application 10 2004 020 463.2. According to this disclosure it is possible, with the assistance of a single active ingredient release regulator, to reduce dosage by varying amounts and/or to administer the active ingredient with tailored release of the active ingredient adapted to the needs of the patient.

Furthermore, a system is also described as an active ingredient release system for systemic or topical release of an active ingredient through and/or onto the skin of a human or animal organism which comprises a plaster containing an active ingredient and an active ingredient release regulator. Preferably, this release regulator is an optionally divisible, active ingredient-impermeable active ingredient release regulator or an optionally divisible active ingredient release regulator which delays active ingredient release, separate from the plaster.

Such active ingredient release systems are not simple for all patients to handle since, in order to achieve exact dosage of the active ingredient, the active ingredient release regulator has to be placed exactly to the required extent on the active ingredient-containing surface of the plaster. Since for this purpose inter alia the adhesive layer of the active ingredient release regulator has also to be exposed, this may easily lead to the regulator becoming stuck together or stuck at least in part to areas of the plaster not containing the active ingredient through improper handling of the active ingredient release regulator.

The object of the present invention was accordingly to provide an application system for active ingredient release systems comprising an active ingredient-containing plaster and an active ingredient release regulator which virtually rules out incorrect positioning of the active ingredient release regulator on the active ingredient-containing layer of the plaster and simplifies handling for all patients and/or care staff.

This object is achieved by provision of the application system according to the invention for an active ingredient release system, comprising a film-form strip, an active ingredient-containing plaster bonded detachably thereto and an active ingredient release regulator, likewise bonded detachably thereto and separate from the active ingredient-containing plaster, the film-form strip comprising a fold line corresponding to its width and having a width which corresponds at least to the width of the active ingredient-containing plaster and to a width optionally extending therebeyond of a peelable protective film used to cover the adhesive surface of the active ingredient-containing plaster, and the length of the strip being a multiple of the length of the plaster, the active ingredient release regulator being positionable after removal of the protective film peelable therefrom on the active ingredient-containing surface of the plaster after removal of its protective film by folding the strip back together along the fold line and the plaster provided with the active ingredient release regulator being applicable directly to the skin with removal of the strip.

The film-form strip (application strip) has preferably to be folded from transparent plastics film which is sufficiently flexible.

Preferably, at least the surface of the application strip on which the active ingredient release regulator is fixed is such that it has abherent properties.

The application system according to the invention comprises the active ingredient-containing plaster and the active ingredient release regulator on the same surface of the application strip. In this case, these two elements are positioned at such a distance from the fold line of the application strip that, upon folding along the fold line of the application strip, the active ingredient release regulator is positioned on the active ingredient-containing surface of the plaster.

The application system according to the invention is additionally distinguished in that the two parts of the application strip, which are foldable against one another by means of the fold line or are folded against one another prior to application of the transdermal system, have at least such differing lengths that, starting from the fold line, a part of the strip which is bonded detachably to the active ingredient release regulator covers at least the entire surface area of the active ingredient release regulator.

In a further embodiment of the application system, the two parts of the application strip which are foldable against one another by means of the fold line are of identical length.

The width of the application strip corresponds at least to the total width of the active ingredient-containing plaster, the application strip preferably being at least 10% wider than the active ingredient-containing plaster, in order in this way to simplify positioning of the active ingredient-containing plaster on the application strip.

The application system according to the invention is distinguished in that both the active ingredient release regulator and the active ingredient-containing plaster are covered with a peelable protective film. This peelable protective film preferably comprises a peel aid, which preferably takes the form of a line of weakness or dividing line in the protective film. If a dividing line is present in the protective film, the part of the protective film not joined to the rest of the protective film is regarded as a peel aid. The line of weakness or dividing line in the protective film is preferably applied parallel to the fold line of the application strip. It is also possible to make the protective film of the active ingredient-containing plaster and the protective film of the active ingredient release regulator from different materials.

As already stated, the active ingredient release regulator is such that it is impermeable to the active ingredient or regulates, i.e. delays, active ingredient release.

Preferably, the optionally divisible active ingredient release regulator impermeable to active ingredient has the following layer structure:
 a) an outer, detachable protective layer
 b) an adhesive layer
 c) an active ingredient barrier layer
 d) a further adhesive layer, which is bonded detachably to the application strip.

This further adhesive layer assists in bonding to the patient's skin.

Once the outer, detachable protective layer has been peeled off both from the plaster and from the active ingredient release regulator, the active ingredient-containing area of the plaster is covered in part, to the desired extent, by means of the active ingredient release regulator by folding together of the application strip. Counterpressure and the peel aid of the protective layer prevent the plaster and/or the active ingredient release regulator from possibly also becoming detached from the application strip upon peeling off of the protective film. If the active ingredient release regulator impermeable to the active ingredient is divisible, i.e. contains a perforation line or line of weakness through the entire active ingredient release regulator, the active ingredient release regulator may be divided prior to removal of the outer, detachable protective layer a) by folding the application strip in the area of this line of weakness and the part of the active ingredient release regulator divided off in this way may be removed altogether from the application strip by peeling. Only then is the outer, detachable protective layer removed both from the active ingredient-containing plaster and from the active ingredient release regulator and the two elements are brought together by folding of the application strip along the fold line and folding together of the two parts of the application strip.

In a preferred embodiment, however, the active ingredient release regulator impermeable to active ingredient is already of a size corresponding to the active ingredient-containing area of the plaster which is to be covered for dosage of active ingredient release, i.e. for establishing reduced dosage of the active ingredient. To this end, the size of the active ingredient release regulator impermeable to active ingredient is so adjusted that in each case 10 to 90% of the active ingredient-containing surface area of the active ingredient-containing plaster is covered.

Alternatively, the active ingredient release regulator may be an optionally divisible active ingredient release regulator which merely delays active ingredient release. Preferably, this active ingredient release regulator is multilayered and has the following layer structure:
 a') an outer, detachable protective layer
 b') an adhesive layer optionally delaying active ingredient release
 c') a layer optionally further delaying active ingredient release and
 d') a further adhesive layer bonded detachably to the application strip.

In a particularly preferred embodiment, the multilayer active ingredient release regulator which delays active ingredient release has the following layer structure:
 a') an outer, detachable protective layer
 b') an adhesive layer
 c') a layer delaying active ingredient release and
 d') a further adhesive layer, which is bonded detachably to the application strip and is bonded to the patient's skin upon application.

If the two adhesive layers b') and d') of the active ingredient release-delaying active ingredient release regulator are together thick enough, they may together function as the release-delaying layer without an active ingredient release-delaying layer c'). Preferably, such an optionally divisible, active ingredient release-delaying active ingredient release regulator then comprises an outer, detachable protective layer a') and an adhesive layer b') and d') which delays active ingredient release and is bonded detachably to the application strip and applied to the patient's skin.

Prior to application onto the patient's skin, the protective film is removed both from the plaster and from the active ingredient release regulator, which latter brings about delayed release of the active ingredient, and the active ingredient release regulator is placed on the active ingredient-containing area of the plaster by folding the application strip along the fold line of the active ingredient release regulator. Counterpressure and the peel aid of the protective layer prevent the plaster and/or the active ingredient release regulator from possibly also becoming detached from the application strip upon peeling off of the protective film.

If the active ingredient release regulator is provided with an active ingredient release-delaying layer and is divisible, the active ingredient release regulator is preferably divided prior to peeling off of the outer protective layer. As stated above, this may take place along the lines of weakness, such as perforations or dividing lines through the entire active ingredient release regulator, provided for possible division, by folding along these dividing lines and peeling off a divided-off part of the active ingredient release regulator. Only then is the outer protective film peeled off the active ingredient release regulator and off the active ingredient-containing plaster and the two parts of the application strip are folded along the fold line for application of the active ingredient release regulator onto the active ingredient-containing area of the plaster.

The size of an active ingredient release regulator delaying the active ingredients may constitute up to 100% of the active ingredient-containing area of a plaster. In a preferred embodiment, coverage is 100%. If coverage is less than 100%, a plaster is obtained with differently delayed release of the active ingredient, i.e. a delayed-release and conventional active ingredient release rate.

Both the active ingredient-containing plaster and the active ingredient release regulator may exhibit any desired shape, size and colour. For example, they may mutually independently have a round, oval, rectangular or other, irregular shape. Preferably the plaster, in particular the active ingredient-containing area of the plaster and the active ingredient release regulator, have mutually matching, preferably identical, shapes.

Preferably, the parts of a divisible active ingredient release regulator which may be separated from one another are marked differently to distinguish them. This marking for the purpose of distinction may comprise different colouring and/or coding of the parts separable from one another.

The active ingredient release system with application strip is suitable for the application of any administrable active ingredient. Preferably, the active ingredient release system is suitable for the transdermal and/or topical administration of active ingredients of any type, particularly preferably of pharmaceutically active ingredients of any type. In particular, the plaster is suitable for transdermal and/or topical release of at least one pharmaceutically active ingredient from the group comprising analgesics, local anaesthetics, hormones, contraceptives, vaccines, immunomodulators, antiallergic agents, antihistamines, cardiac preparations, antihypertensive agents, psychopharmaceuticals, antirheumatic agents and enzymes, preferably for the administration of at least one pharmaceutically active ingredient selected from the group comprising narcotic analgesics, opioids, tranquillisers, preferably benzodiazepines, stimulants and other narcotics.

The application system according to the invention is particularly preferably suitable for the administration of at least one transdermally administrable opioid, tranquilliser or of another narcotic, which is selected from the group comprising N-{1-[2-(4-ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methylphenethylamine (amphetamine), 2-(α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo[4,3-a][1,4]diazepine (brotizolam), 17-cyclopropylmethyl-4,5α-epoxy-7α[(S)-1-hydroxy-1,2,2-trimethylpropyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl) dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one (clotiazepam), 10-chloro-11b-(2-chlorophenyl)-2,3,7,11b-tetrahydrooxazolo[3,2-d][1,4]benzodiazepin-6(5H)-one (cloxazolam), (−)-methyl-[3β-benzoyloxy-2β(1αH, 5αH)-tropane carboxylate] (cocaine), 4,5α-epoxy-3-methoxy-17-methyl-7-morphinen-6α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphene), dextromethorphan, dezocine, diampromide, diamorphine, 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6a-morphinandiol (dihydromorphine), dimenoxadol, dimepheptanol, dimethylthiambutene, dioxaphetyl butyrate, dipipanone, (6aR,10aR)-6,6,9-trimethyl-3-pentyl-6a,7,8,10α-tetrahydro-6H-benzo[c]chromen-1-ol (dronabinol), eptazocine, 8-chloro-6-phenyl-4H-[1,2,4]triazolo[4,3-(a)][1,4]benzodiazepine (estazolam), ethoheptazine, ethylmethylthiambutene, ethyl[7-chloro-5-(2-fluorophenyl)-2,3-dihydro-2-oxo-1H-1,4-benzodiazepine-3-carboxylate] (ethyl loflazepate), 4,5α-epoxy-3-ethoxy-17-methyl-7-morphinen-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine(fencamfamine), 7-[2-α-methylphenethylamino)ethyl]-theophylline) (fenethyl)ine), 3-α-methylphenethylamino)propionitrile (fenproporex), N-(1-phenethyl-4-piperidyl)propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethylmorphinan, 11-chloro-8,12b-dihydro-2,8-dimethyl-12b-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol (LAAM)), (−)-6-dimethylamino-4,4-diphenol-3-heptanone (levomethadone), (−)-17-methyl-3-morphinanol (levorphanol), levophenacylmorphane, levoxemacin, lofentanil, 6-(2-chlorophenyl)-2-(4-methyl-1-piperazinylmethylene)-8-nitro-2H-imidazo[1,2-a][1,4]-benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine(mefenorex), meperidine, 2-methyl-2-propyltrimethylene dicarbamate (meprobamate), meptazinol, metazocine, methylmorphine, N,α-dimethylphenethylamine(methamphetamine), (±)-6-dimethylamino-4,4-diphenol-3-heptanone (methadone), 2-methyl-3-o-tolyl-4(3H)-quinazolinone (methaqualone), methyl[2-phenyl-2-(2-piperidyl)acetate](methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide(modafinil), 4,5α-epoxy-17-methyl-7- morphinen-3,6α-diol (morphine), myrophine, (±)-trans-3-(1,1-dimethylheptyl)-7,8,10,10α-tetrahydro-1-hydroxy-6,6-dimethyl-6H-dibenzo-[b,d]pyran-9(6αH)-one (nabilone), nalbuphene, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation from the plants belonging to the species *Papaver somniferum* (opium), 7-chloro-3-hydroxy-5-phenyl-1H-1,4-benzodiazepin-2(3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies *setigerum*), papavereturn, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl-(1-methyl-4-phenyl-4-piperidinecarboxylate) (pethidine), phenadoxone, phenomorphane, phenazocine, phenoperidine, piminodine, pholcodeine, 3-methyl-2-phenylmorpholine (phenmetrazine), 5-ethyl-5-phenylbarbituric acid (phenobarbital), α,α-dimethylphenethylamine(phentermine), 7-chloro-5-phenyl-1-(2-propynyl)-1H-1,4-benzodiazepin-2(3H)-one (pinazepam), α-(2-piperidyl)benzhydryl alcohol (pipradrol), 1'-(3-cyano-3,3-diphenylpropyl)[1,4'-bipiperidine]-4'-carboxamide(piritramide), 7-chloro-1-(cyclopropylmethyl)-5-phenyl-1H-1,4-benzodiazepin-2(3H)-one (prazepam), paramethadione, profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido)piperidino]propanoate}(remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepin-2(3H)-one (tetrazepam), ethyl (2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R*,2R*)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3-(3-methoxyphenyl)-2-methyl-pentan-3-ol, (1RS,3RS,6RS)-6-dimethylaminomethyl-1-(3-methoxyphenyl)-cyclohexane-1,3-diol, 3-(2-dimethylaminomethyl-1-hydroxy-cyclohexyl)-phenyl 2-(4-isobutyl-phenyl)-propionate, 3-(2-dimethylaminomethyl-1-hydroxy-cyclohexyl)phenyl 2-(6-methoxy-naphthalen-2-yl)-propionate, 3-(2-dimethylaminomethyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester together with corresponding stereoisomeric compounds, in each case the corresponding derivatives thereof, in particular amides, esters or ethers, and in each case the physiologically acceptable compounds thereof, in particular the salts and solvates thereof, particularly preferably hydrochlorides.

The compounds (1R*,2R*)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol or the stereoisomeric compounds thereof or the physiologically acceptable compounds thereof, in particular the hydrochlorides thereof, the derivatives thereof, such as esters, ethers or amides, and processes for the production thereof are known, for example, from EP-A-693 475 or EP-A-780 369. The corresponding descriptions are hereby introduced as a reference and are deemed to be part of the disclosure.

Opioids are preferably used as pharmaceutically active ingredients to be administered transdermally. These active ingredients are very particularly preferably selected from the group comprising morphine, oxycodone, buprenorphine and fentanyl, the derivatives thereof, preferably esters, ethers or amides, or the in each case physiologically acceptable compounds thereof, preferably the salts or solvates thereof, particularly preferably the hydrochlorides thereof. Use of the free base is particularly preferred.

Preferably, the concentration of the active ingredient is at saturation concentration or slightly below, since this promotes release onto the skin. This saturation concentration may be determined by routine testing.

The active ingredient barrier layer of the active ingredient release regulator preferably consists of a polymer such as polyester, e.g. polyethylene terephthalate, polyolefin, such as polyethylene, polypropylene or polybutylene, polycarbonate, polyethylene oxide, polyurethane, polystyrene, polyamide, polyimide, polyvinyl acetate, polyvinyl chloride, polyvinylidene chloride, and/or copolymers of for example acrylonitrile/butadiene/styrene. The thickness of the layer is preferably 5 to 25 μm.

The active ingredient release-delaying layer of an active ingredient release regulator may consist of a film-forming polymer selected from the group comprising cellulose derivatives, such as ethylcellulose, hydroxypropylcellulose or carboxymethylcellulose, polyethylenes, chlorinated polyethylenes, polypropylenes, polyurethanes, polycarbonates, polyacrylic acid esters, polyacrylates, polymethacrylates, polyvinyl alcohols, polyvinyl chlorides, polyvinylidene chlorides, polyvinylpyrrolidones, polyethylene terephthalates, polytetrafluoroethylenes, ethylene/propylene copolymers, ethylene/ethyl acrylate copolymers, ethylene/vinyl acetate copolymers, ethylene/vinyl alcohol copolymers, vinyl chloride/vinyl acetate copolymers, vinylpyrrolidone/ethylene/vinyl acetate copolymers, rubbers, rubber-type synthetic homo-, co- or block polymers, silicones, silicone derivatives and mixtures thereof.

The active ingredient release-delaying layer may preferably comprise a layer based on an ethylene/vinyl acetate copolymer or a polyacrylate or a combined layer of the two adhesive layers b') and d') without a separate, active ingredient release-delaying layer, which delays active ingredient release for the predetermined period of plaster use, preferably for 3 to 7 days. Conventional active ingredient reservoir membranes may likewise be used as the release-delaying layer.

The active ingredient-containing plaster may take the form of a reservoir or matrix system (Bauer K. H., Frömming K.-H., Führer C., Pharmazeutische Technologie [Pharmaceutical Technology], pages 381-383; Müller R. H., Hildebrand G. E., Pharmazeutische Technologie Moderne Arzneiformen [Pharmaceutical Technology: Modern Dosage Forms], Chapter 8).

In accordance with the matrix system, the active ingredient-containing plaster may preferably comprise a backing layer, an active ingredient-containing layer and an adhesive layer, wherein the active ingredient-containing layer may simultaneously be the adhesive layer, in which the active ingredient is present dissolved and/or dispersed in a matrix together with the adhesive. The active ingredient-containing plaster comprises an outer, detachable protective layer.

Adhesives which may be used for the adhesive layer of the plaster and of the active ingredient release regulator are preferably pressure-sensitive adhesives. Examples of polymers which are suitable for this purpose are polyacrylates, polyvinyl ethers, polyisobutylenes (PIB), styrene/isoprene or butadiene/styrene copolymers or polyisoprene rubbers. Silicone adhesives, such as for example optionally crosslinked polydimethylsiloxanes, are furthermore suitable. Plastics based on esters of glycines, glycerol or pentaerythritol, or hydrocarbons, such as polyterpenes, are also suitable. Polyacrylate-based adhesives are produced by polymerisation of acrylates, methacrylates, alkyl acrylates and/or alkyl methacrylates, with optionally further $\alpha,\beta$-unsaturated monomers, such as acrylamide, dimethylacrylamide, dimethylaminoethyl acrylate, hydroxyethyl acrylate, hydroxypropyl acrylate, methoxyethyl acrylate, methoxyethyl methacrylate, acrylonitrile and/or vinyl acetate. Using these pressure-sensitive adhesives, the backing layer or cover layer of the plaster may be bonded to the application strip at least at points, preferably over the entire surface.

The adhesive layers of the plaster and of the active ingredient release regulator may also contain skin penetration promoters, fillers (such as zinc oxide or silica), crosslinking agents, antioxidants and/or solvents. The thickness of the adhesive layers is preferably in each case 3 to 100 μm.

The backing layer or cover layer of the plaster is preferably impermeable to and inert towards the substances contained in the active ingredient-containing layer and in the adhesive layer, in particular towards the active ingredient to be released transdermally and/or topically, and may be based on polymers, such as polyester, for example polyethylene terephthalate; polyolefins, such as polyethylenes, polypropylenes or polybutylenes; polycarbonates; polyethylene oxides, polyurethanes, polystyrenes, polyamides, polyimides, polyvinyl acetates, polyvinyl chlorides, polyvinylidene chlorides and/or copolymers such as acrylonitrile/butadiene/styrene copolymers and or mixtures thereof optionally containing paper fibres and/or textile fibres, which may if necessary be metallised or pigmented. The backing layer or cover layer of the plaster may also consist of a combination of metal foil and polymer layer. The thickness of the backing layer is preferably 3 to 100 μm.

To fix the plaster to the application strip, the strip comprises a layer of pressure-sensitive adhesive on the surface thereof at least in the peripheral area of the plaster. Fixing may also be achieved using a double adhesive strip.

The active ingredient-containing matrix layer of the plaster may contain matrix-forming polymers, skin penetration promoters, solubilising agents, crosslinking agents, stabilisers, emulsifiers, preservatives, thickeners and/or further conventional auxiliaries.

The matrix-forming polymer used is preferably at least one film-forming polymer selected from among the group comprising hydroxypropylcellulose, carboxymethylcellulose, polyethylenes, chlorinated polyethylenes, polypropylenes, polyurethanes, polycarbonates, polyacrylic acid esters, polyacrylates, polymethacrylates, polyvinyl alcohols, polyvinyl chlorides, polyvinylidene chlorides, polyvinylpyrrolidones, polyethylene terephthalates, polytetrafluoroethylenes, ethylene/propylene copolymers, ethylene/ethyl acrylate copolymers, ethylene/vinyl acetate copolymers, ethylene/vinyl alcohol copolymers, ethylene/vinyloxyethanol copolymers, vinyl chloride/vinyl acetate copolymers, vinylpyrrolidone/ethylene/vinyl acetate copolymers, rubbers, rubber-like synthetic homopolymers, copolymers or block polymers, silicones, silicone derivatives, preferably siloxane/methacrylate copolymers, cellulose derivatives, preferably ethylcellulose or cellulose ethers and mixtures thereof. If the active ingredient-containing layer is simultaneously the adhesive layer, it preferably contains, apart from at least one of the enumerated polymers, at least one of the above-listed adhesives.

The solubilising agents used may comprise N-methyl-2-pyrrolidone, laurylpyrrolidone, triethanolamine, triacetin, diethylene glycol-monoethyl ether, derivatives of fatty acids or fatty alcohols, low molecular weight, polyhydric alcohols such as for example propylene glycol or glycerol and/or surfactant compounds.

If the active ingredient-containing plaster is built up in accordance with the reservoir system, the reservoir membrane may consist of inert polymers such as for example polyethylenes, polypropylenes, polyvinyl acetates, polyamides, ethylene/vinyl acetate copolymers and/or silicones. Just the reservoir membrane itself may provide controlled release of the active ingredient from the reservoir.

The active ingredient-containing matrix or the active ingredient-containing reservoir of the plaster may also contain solvents, such as for example water, ethanol, 1-propanol, isopropanol, a low molecular weight, polyhydric alcohol, for example propylene glycol or glycerol, or an ester, such as isopropyl myristate, surfactant compounds or mixtures thereof.

Stabilisers which may be used for the active ingredient-containing matrix or for the content of the active ingredient-containing reservoir are antioxidants, such as vitamin E, butylhydroxytoluene, butylhydroxyanisole, ascorbic acid, ascorbyl palmitate, and/or chelating agents, such as for example disodium ethylenediaminetetraacetic acid, potassium citrate or sodium citrate.

The active ingredient-containing matrix or the active ingredient-containing reservoir may also contain conventional skin penetration promoters.

The plaster may also contain in one or more layers at least one plasticiser or skin penetration promoter selected from among the group comprising long-chain alcohols, such as dodecanol, undecanol, octanol, esters of carboxylic acids with polyethoxylated alcohols, diesters of aliphatic dicarboxylic acids, such as adipic acid, and medium-chain triglycerides of caprylic acid and/or capric acid, coconut oil, polyhydric alcohols, such as 1,2-propanediol, esters of polyhydric alcohols, such as glycerol with laevulinic acid or caprylic acid, and etherified polyhydric alcohols.

The outer, detachable protective layer of the plaster and the outer, detachable protective layer of the active ingredient release regulator, which may be identical in size to the application strip and may be bonded detachably to the plaster, the active ingredient release regulator and the surface of the application strip not covered thereby, may consist of polyethylene, polyester, polyethylene terephthalate, polypropylene, polysiloxane, polyvinyl chloride or polyurethane and optionally of treated paper fibres, such as for example cellophane, and optionally comprise at least one silicone, fluorosilicone or fluorocarbon coating.

Production of the active ingredient release regulator according to the invention or of the plaster may proceed in accordance with known production processes comprising process steps such as lamination, coextrusion, stamping, delamination, unwinding, cutting, rewinding, assembly or dispensing (Verpackungs-Rundschau, 4/2002, 83-84).

FIG. 1 shows an application system (1) according to the invention for an active ingredient release system, comprising a film-form application strip (2), an active ingredient-containing plaster (3) bonded detachably thereto, which comprises an active ingredient-containing area (4), and an active ingredient release regulator (6) separate from the plaster, which may be bonded to the active ingredient-containing area of the plaster via a fold line (5) of the application strip by folding along the fold line (5) after peeling off of the removable protective film (7) (shown in broken lines) both from the active ingredient-containing plaster and from the active ingredient release regulator.

EXAMPLE a) Production of a Plaster Containing Buprenorphine 1139 g of a 48 wt. % polyacrylate solution of a self crosslinking acrylate copolymer prepared from 2-ethylhexyl acrylate, vinyl acetate, acrylic acid (solvent:ethyl acetate:heptane:isopropanol:toluene:acetylacetonate in the ratio 37:26:26:4:1), 100 g of laevulinic acid, 150 g of oleyl acetate, 100 g of polyvinylpyrrolidone, 150 g of ethanol, 200 g of ethyl acetate and 100 g of buprenorphine base were homogenised. The mixture was stirred for approx. two hours and it was visually checked whether all the solids had dissolved. Evaporative loss was additionally checked by reweighing and the loss of solvent was optionally made up by addition of ethyl acetate.

As cover layer, a 420 mm wide, transparent polyester film was coated with the above-described mixture in such a way that the basis weight of the dried adhesive layer was 80 g/m².

The solvent was removed by drying with hot air which was passed over the moist web. The active ingredient-containing adhesive layer was then covered with a 15 μm thick polyester film, which could be peeled off again by silicone treatment. An area corresponding to the intended quantity of active ingredient was stamped out with suitable cutting tools.

b) Production of an Active Ingredient Release Regulator with the Following Layer Structure:
an outer, detachable protective layer
an adhesive layer
an active ingredient barrier layer
an adhesive layer
a detachable protective layer for fixing to the application strip.

To produce the active ingredient release regulator, a polyethylene terephthalate film with a thickness of 75 μm was clamped as active ingredient barrier layer in an Ericsson film coater (Ericsson GmbH & Co. KG, Hemer, Germany), coated with the mixture described under Example 1a) with the exception of buprenorphine and dried for 2 hours, whereby an adhesive layer with a thickness of 90 μm was obtained. This adhesive layer was bonded detachably to the siliconised side of a polyethylene terephthalate-based film siliconised on one side.

The procedure was repeated for the still bare second surface of the active ingredient barrier layer, such that the active ingredient barrier layer had on both sides an adhesive layer with a thickness of 90 μm and a protective layer bonded detachably thereto.

By means of a suitable stamping tool, the active ingredient release regulator was stamped out with a size corresponding to half the size of the plaster produced according to Example 1a).

c) On a strip of transparent polyester film, foldable along a fold line into two parts of equal size, there were fixed on either side of the fold line on the same surface on the one hand the plaster produced according to 1a) and on the other hand the active ingredient release regulator produced according to 1b). The arrangement of the two elements of the transdermal release system corresponds to that shown in FIG. 1. To fix the plaster in place, the application strip was provided in the area of the plaster to be fixed with a layer of pressure-sensitive adhesive. Fixing in place of the active ingredient release regulator took place, after peeling off of one of the outer, detachable protective layers of the release regulator, by means of the thereby exposed adhesive layer.

Preferably, the outer, detachable protective layers remaining in each case may also additionally be peeled off the plaster and the active ingredient release regulator and the entire surface of the application strip provided with the plaster and the release regulator may be covered with a detachable, metallised protective film with peel aid.

Preferably, the application system according to the invention may be folded by means of the fold line and preferably marketed in a sterile and/or gas-tight packaging.

The invention claimed is: The invention claimed is:

1. An application system for an active ingredient release system, said application system comprising a carrier film strip, an active ingredient-containing plaster detachably affixed to said strip, and an active ingredient release regulator also detachably affixed to said strip, said release regulator being separate from the active ingredient-containing plaster; said carrier film strip having a fold line across the width thereof between the active ingredient containing plaster and the active ingredient release regulator and having a width at least as wide as the active ingredient-containing plaster and at least as wide as a peelable protective film which covers an adhesive surface of the active ingredient-containing plaster, and said carrier film strip having a length which is a multiple of the length of the active ingredient-containing plaster; wherein:
after removal of a peelable cover film from the active ingredient release regulator and of the protective film which covers the adhesive surface of the active ingredient-containing plaster, the active ingredient release regulator is permanently positionable on the adhesive surface of the active ingredient-containing plaster by folding the strip together along the fold line, and then the plaster provided with the active ingredient release regulator can be applied directly to the skin of a user with detachment of the strip from the plaster;
and wherein:
the active ingredient release regulator is impermeable to active ingredient or retards active ingredient release and has the following layer structure:
a') an outer, detachable protective layer;
b') an adhesive layer optionally retarding active ingredient release;
c') optionally a layer optionally further retarding active ingredient release, and d') a further adhesive layer bonded detachably to the strip.

2. An application system according to claim 1, wherein the strip is comprised of a transparent synthetic resin film.

3. An application system according to claim 1, wherein at least the surface of the strip to which the active ingredient release regulator is affixed has bond release properties.

4. An application system according to claim 1, wherein the active ingredient-containing plaster and the active ingredient release regulator are positioned on the same surface of the strip and are each spaced a distance from the fold line such that when the strip is folded along the fold line, the active ingredient release regulator is positioned on the surface of the active ingredient-containing plaster.

5. An application system according to claim 1, wherein the active ingredient release regulator and the active ingredient-containing plaster are both covered with an outer, peelable protective film.

6. An application system according to claim 5, wherein the protective film is provided with a release aid.

7. An application system according to claim 6, wherein said release aid comprises a line of weakness in the protective film or a part of the protective film not joined to the rest of the protective film.

8. An application system according to claim 1, wherein the protective film which covers the active ingredient-containing plaster and the protective film over the active ingredient release regulator are made of different materials.

9. An application system according to claim 1, wherein when the strip is folded along the fold line, the two parts of the folded strip have differing lengths such that the part of the strip detachably affixed to the active ingredient release regulator covers at least the entire surface area of the active ingredient release regulator.

10. An application system according to claim 1, wherein when the strip is folded along the fold line, the two parts of the folded strip are of identical length.

11. An application system according to claim 1, wherein the optionally divisible, active ingredient-impermeable active ingredient release regulator is multilayered and has the following layer structure:
    a) an outer, detachable protective layer
    b) an adhesive layer
    c) an active ingredient barrier layer
    d) a further adhesive layer, which is detachably affixed to the strip.

12. An application system according to claim 1, wherein the adhesive layers b') and d') together sufficiently retard release of the active ingredient that a layer c') further rearding active ingredient release is unnecessary.

13. An application system according to claim 1, wherein the active ingredient release regulator is rendered divisible by a pre-formed separation aid selected from the group consisting of lines of weakness, lines of perforations, and cut lines.

14. An application system according to claim 1, wherein the active ingredient release regulator is impermeable to the active ingredient and is divisible such that from 10 to 90% of the surface of the active ingredient-containing plaster is uncovered.

15. An application system according to claim 1, wherein the active ingredient release regulator is impermeable to the active ingredient and corresponds in size to from 10 to 90% of the surface of the active ingredient-containing plaster.

16. An application system according to claim 1, wherein the active ingredient release regulator has a size corresponding to from 10 to 100% of the surface of the active ingredient-containing plaster.

17. An application system according to claim 1, wherein the plaster comprises an active ingredient-containing reservoir or an active ingredient-containing matrix.

18. An application system according to claim 1, wherein the application system is packaged in a folded condition in a package with said strip folded along the fold line.

* * * * *